United States Patent [19]

Ogata

[11] 4,285,738

[45] Aug. 25, 1981

[54] CLEANING COMPOSITION FOR CONTACT LENSES

[75] Inventor: Kazumi Ogata, Toyonaka, Japan

[73] Assignee: Senju Pharmaceutical Co., Ltd., Osaka, Japan

[21] Appl. No.: 29,993

[22] Filed: Apr. 16, 1979

[30] Foreign Application Priority Data

Apr. 24, 1978 [JP] Japan ................................ 53/48392

[51] Int. Cl.³ ............................................... B08B 3/08
[52] U.S. Cl. ......................................... 134/26; 134/28; 134/42; 252/105; 252/174.12; 252/523; 252/525; 252/541; 252/544; 252/DIG. 12
[58] Field of Search ...................... 134/2, 3, 42, 26, 28; 252/105, 174.12, 523, 525, 541, 544, DIG. 12

[56] References Cited

U.S. PATENT DOCUMENTS

| | | | |
|---|---|---|---|
| 3,149,042 | 9/1964 | Habicht et al. | 252/105 X |
| 3,627,683 | 12/1971 | Adam et al. | 252/DIG. 12 X |
| 3,635,797 | 1/1972 | Battistoni et al. | 252/174.12 X |
| 3,741,901 | 6/1973 | Ziffer | 252/105 X |
| 3,908,680 | 9/1975 | Krezanoski | 134/42 X |
| 3,910,296 | 10/1975 | Karageozian et al. | 134/42 X |
| 3,954,965 | 5/1976 | Boghosian et al. | 424/81 |
| 4,115,292 | 9/1978 | Richardson et al. | 252/DIG. 12 X |

FOREIGN PATENT DOCUMENTS 1587950  4/1970  France .............................. 252/DIG. 12

*Primary Examiner*—Marc L. Caroff
*Attorney, Agent, or Firm*—Burgess, Ryan & Wayne

[57] ABSTRACT

Proteinaceous matter lodged on the surface of a contact lens is removed in a short period of time by immersion of the lens in an aqueous hypertonic composition containing urea or a salt of guanidine and a reducing agent such as a sulfite, a pyrosulfite, etc. The cleaning effect of the composition increases markedly by addition of a proteolytic enzyme even in an amount not effective when the enzyme is used in the absence of urea or a guanidine salt.

10 Claims, No Drawings

CLEANING COMPOSITION FOR CONTACT LENSES

The present invention relates to a cleaning composition, and more particularly, to a new and useful cleaning composition for removing proteinaceous deposits from contact lenses.

There are three kinds of contact lenses; hard contact lenses based on methyl methacrylate, soft contact lenses based on, for example, 2-hydroxyethyl methacrylate or cellulose acetate butyrate (CAB), and silicone contact lenses based on a polysiloxane-type hydrophobic material.

In contrast to hard contact lenses, soft and silicone contact lenses are soft in nature, have superior permeability to oxygen and give less "foreign" sensations to novice users, and therefore have been widely used in recent years.

On prolonged usage, these contact lenses tend to become contaminated and soiled, particularly by bacteria and with deposits of ocular fats and proteinaceous matter, which in turn make contact lenses opaque, causing injuries to eyes. Particularly, ocular fats and proteinaceous matter which are utilized by bacteria as nutrients for growth and multiplication should be removed. Ocular fats may be substantially removed by a generally used conventional contact lens cleaning composition based on a surfactant, but proteinaceous matter is anchored to contact lenses and may not be removed by a conventional cleaning composition. Particularly, in the case of soft contact lenses, disinfection by boiling further denatures and coagulates such proteinaceous matter, which will be anchored to contact lenses more firmly, thus making removal of proteinaceous matter very difficult.

It is considered that most of such proteineous matter is formed by lysozyme in the lachrymal fluid, and lodgement of such proteinaceous matter on contact lenses shortens the useful lives of contact lenses.

As a cleaning composition for rejuvenating contact lenses contaminated with proteinaceous matter, there has been disclosed a cleaning composition comprising a proteolytic enzyme and a hydrosulfohydryl compound in U.S. Pat. No. 3,910,296. Such a known cleaning composition is effective in cleaning contact lenses, but requires a very time-consuming cleaning operation.

The inventor has devoted himself to research for removal of proteinaceous matter lodged on contact lenses and finally found a contact lens cleaning composition capable of readily removing such proteinaceous matter.

It is therefore an object of the present invention to provide a contact lens cleaning composition useful for removing proteinaceous matter lodged on contact lenses.

An aspect of the present invention relates to a cleaning composition for contact lenses comprising urea and/or an acid salt of guanidine, and, as a reducing agent, a sulfite, a pyrosulfite, a dithionite or sodium borohydride or a reducing organic water-soluble mercapto group-containing compound.

Proteinaceous deposits on contact lenses may readily be dissolved out only by immersion of the lenses in a hypertonic aqueous solution of the contact lens cleaning composition in accordance with the present invention. There may be a case where such a cleaning composition is preferably heated. Immersion for 1 to 5 hours may be sufficient.

In accordance with the present invention, urea and/or an acid salt of guanidine is used in an amount sufficient to make a hypertonic aqueous solution. An examples of said acid salt of guanidine, there may be mentioned the hydrochloride, hydrobromide and hydroiodide of guanidine. Urea may be used in concentrations from 5 W/V% through saturation, preferably 20 W/V% to 60 W/V%. The acid salt of guanidine may be used in concentrations from 3 W/V% through saturation, preferably 20 W/V% to 60 W/V%.

The reducing agent may be used only in effective concentrations to reduce the intermolecular or intramolecular S-S bonds in the contaminant proteinaceous matter, generally from 0.01 W/V% to 20 W/V% and preferably 0.1 W/V% to 10 W/V%.

Sulfites, pyrosulfites and dithionites to be used include the alkali metal salts or alkaline earth metal salts of sulfurous acid, pyrosulfurous acid and dithioneous acid, e.g. lithium, sodium, calcium and magnesium salts.

The reducing water-soluble mercapto compounds include SH(group)-containing water-soluble lower alcohols, organic carboxylic acids, organic amines and salts thereof, amino acids and di- or tripeptides, e.g. cysteine, acetylcysteine, cysteine hydrochloride ethyl ester, glutathione, homocysteine, carbamoyl cysteine, cystenylglycine, 2-mercaptopropionic acid, 2-mercaptopropionylglycine, 2-mercaptoethanol, 2-mercaptoethylamine hydrochloride, etc.

The above-mentioned materials may be used as dissolved in sterile water.

A description will now be made of the effectiveness of the cleaning composition of the present invention for removal of proteinaceous matter lodged on contact lenses, together with test data.

Tests were performed in the following manner.

Each of the soft contact lenses contaminated with egg white lysotium as disclosed in Japanese Patent Public Disclosure No. SHO 50-31834 (corresponds to U.S. Pat. No. 3,910,296) was immersed in each (5 ml) of the cleaning compositions shown in Table 1, for about 5 to 30 minutes at room temperature or under heating, rubbed gently with fingers, then rinsed and allowed to stand in physiological saline solution. Thereafter, the lenses were examined by the naked eye for the degree of desoiling.

TABLE 1

|  |  | Reducing agent |  | Evaluation index of lens after treatment |
|---|---|---|---|---|
| (Part I) |  |  |  |  |
| 1. Guanidine hydrochloride | 50(W/V)% | Sodium hydrogen-sulfite | 2(W/V)% | +++ |
| 2. Guanidine hydrobromide | " | Sodium hydrogen-sulfite | " | +++ |

TABLE 1-continued

|   | | Reducing agent | | Evaluation index of lens after treatment |
|---|---|---|---|---|
| 3. Guanidine hydroiodide | " | Sodium hydrogen-sulfite | " | +++ |
| 4. Urea | " | Sodium hydrogen-sulfite | " | +++ |
| 5. Urea | " | Calcium sulfite | " | +++ |
| 6. Urea | " | Sodium hydrogen-sulfite | " | +++ |
| (Part II) | | | | |
| 7. Urea | " | Sodium metabisulfite | " | +++ |
| 8. Urea | " | Cysteine | " | +++ |
| 9. Urea | " | Acetylcysteine* | " | +++ |
| 10. Urea | " | Cysteine hydrochloride ethylester | " | +++ |
| 11. Urea | " | Glutathione* | " | +++ |
| 12. Urea | " | Homocysteine | " | +++ |
| 13. Urea | " | Carbamoylcysteine* | " | +++ |
| 14. Urea | " | Cystenylglycine | " | +++ |
| 15. Urea | " | 2-Mercaptopropionic acid* | " | +++ |
| 16. Urea | " | 2-Mercaptopropionylglycine* | " | +++ |
| 17. Urea | " | 2-Mercaptoethanol | " | +++ |
| 18. Urea | " | 2-Mercaptoethylamine hydrochloride | " | +++ |
| 19. Urea | " | Sodium borohydride | " | +++ |
| 20. Urea | " | Ascorbic acid* | " | − |
| 21. Urea | " | Sodium hydrogen-sulfite | 20(W/V)% | +++ |
| 22. Urea | " | Sodium hydrogen-sulfite | 10(W/V)% | +++ |
| 23. Urea | " | Sodium hydrogen-sulfite | 1(W/V)% | +++ |
| 24. Urea | " | Sodium hydrogen-sulfite | 0.1(W/V)% | +++ |
| 25. Urea | " | Sodium hydrogen-sulfite | 0.05(W/V)% | +++ |
| 26. Urea | " | Sodium hydrogen-sulfite | 0.01(W/V)% | +++ |
| 27. Urea | " | Sodium hydrogen sulfite | 0.005(W/V)% | + |
| (Part III) | | | | |
| 28. Urea | " | Not added | | − |
| 29. Urea | Saturated solution | Sodium hydrogen-sulfite | 5(W/V)% | +++ |
| 30. | 60(W/V)% | Sodium hydrogen-sulfite | " | +++ |
| 31. Urea | 40(W/V)% | Sodium hydrogen-sulfite | " | +++ |
| 32. Urea | 30(W/V)% | Sodium hydrogen-sulfite | " | +++ |
| 33. Urea | 20(W/V)% | Sodium hydrogen-sulfite | " | +++** |
| 34. Urea | 10(W/V)% | Sodium hydrogen-sulfite | " | +++** |
| 35. Urea | 5(W/V)% | Sodium hydrogen-sulfite | " | ++** |
| 36. Urea | 1(W/V)% | Sodium hydrogen-sulfite | " | +** |
| 37. Guanidine HCl | 15(W/V)% | Sodium hydrogen-sulfite | " | +++** |
| 38. Guanidine HCl | 7(W/V)% | Sodium hydrogen-sulfite | " | ++** |
| 39. Guanidine HCl | 3(W/V)% | Sodium hydrogen-sulfite | " | +** |
| 40. Not added | | Sodium hydrogen-sulfite | " | −** |

*Neutralized with sodium carbonate
**Under heating at about 100° C.
+++Lens became colorless and clarified with proteineous matter removed
++Lens was substantially clarified with some residue of proteinaceous matter
+Lens was only partially clarified
−Apparently almost unclarified As apparent from the above data, the cleaning composition in accordance with the present invention is As a result of further study by the inventor, it has been found that the cleaning effect of the present composition increases markedly by addition of a proteolytic enzyme involving a synergistic effect between urea or an acid salt of guanidine and the enzyme.

Another aspect of the present invention relates to a contact lens cleaning composition comprising urea and/or an acid salt of guanidine, a sulfhydryl compound and a proteolytic enzyme.

Proteolytic enzymes to be incorporated in the cleaning composition in accordance with the present invention include protease such as papain, trypsin, α-chymotrypsin and proteinase which are decomposable proteinaceous deposit on contact lenses. Such enzymes may be used in concentration from 0.005 (W/V)% to 5 (W/V)%, preferably 0.05 (W/V)% to 1.0 (W/V)%.

Urea and/or an acid salt of guanidine may be used in a hypertonic concentration preferably, from 10 (W/V)% to 60 (W/V)% more preferably 20 (W/V)% to 40 (W/V)%. Acid salts of guanidine to be used for the present invention include the hydrochloride, hydrobromide and hydroiodide.

Sulfohydryl compounds include sodium sulfite, sodium pyrosulfite, hydrochloride, of cysteine and acetylcysteine. The concentration of such compounds need not be more than the range of 0.1 (W/V)% to 5 (W/V)%.

A description will now be made of the effectiveness of the cleaning composition of the present invention for removal of proteinaceous deposits on contact lenses, together with test data.

Tests were performed in the following manner.

Each of the soft contact lenses contaminated with egg white lysozyme as disclosed in Japanese Patent Public Disclosure No. SHO 50-31834 (corresponds to U.S. Pat. No. 3,910,296) was immersed in each of 5 ml cleaning compositions shown in Table 2 (in which the components were dissolved in physiological saline solution) at room temperature for 6 hours, and was rubbed gently with fingers, then rinsed, and allowed to stand in physiological saline solution for 1 hour. Thereafter, the lenses were examined by the naked eye for the degree of desoiling.

As proteolytic enzymes, there were used protease and α-chymotrypsin produced by SIGMA chemical Co., (St. Louis, Mo., U.S.A.), papain and trypsin produced by Wako Pure Chemicals Co., Ltd. (Osaka, Japan), Proteinase (protease from *Bacillus subtilis*) produced by Nakarai Chemical Co., Ltd. (Kyoto, Japan) and Pronase p (protease from *Streptomyces griseus*) produced by Kaken Kagaku Co., Ltd. (Tokyo, Japan).

TABLE 2

| Enzyme | | Protein-denaturant | Sodium hydrogen-sulfite | Evaluation index of lens after treatment |
|---|---|---|---|---|
| Protease | 0.5(W/V)% | Urea 50(W/V)% | 1.0(W/V)% | +++ |
| " | " | Urea 40(W/V)% | " | +++ |
| " | " | Urea 30(W/V)% | " | +++ |
| " | " | Urea 20(W/V)% | " | +++ |
| " | " | Urea 10(W/V)% | " | ++ |
| " | " | Control(not added) | " | + |
| Papain | " | Urea 20(W/V)% | " | +++ |
| " | " | Guanidine hydrochloride 20(W/V)% | " | +++ |
| Proteinase | " | Urea 20(W/V)% | " | +++ |
| " | " | Guanidine hydrochloride 20(W/V)% | " | +++ |
| Trypsin | " | Urea 10(W/V)% + Guanidine hydrochloride 10(W/V)% | " | +++ |
| " | " | Urea 20(W/V)% | " | +++ |
| α-chymotrypsin | " | " | " | +++ |
| Pronase P | 5(W/V)% | " | " | +++ |
| " | 0.5(W/V)% | " | " | +++ |
| " | 0.05(W/V)% | " | " | +++ |
| " | 0.01(W/V)% | " | " | +++ |
| " | 0.005(W/V)% | " | " | +++ |
| " | 0.001(W/V)% | " | " | ++ |
| Control (not added) | | " | " | — |

Each of these cleaning compositions was adjusted to pH 6.5 to 7.0 by 1N-sodium hydroxide.
+++Lens became colorless and clarified with proteineous matter removed.
++Lens was substantially clarified with some residue of proteinaceous matter
+Lens was only partially clarified.
—Apparently almost unclarified.

As apparent from the above data, a cleaning composition comprising a proteolytic enzyme, urea and/or an acid salt of guanidine in the presence of sodium hydrogensulfite, is very effective in the removal of proteinaceous matter lodged on contact lenses.

The effective concentration of the proteolytic enzyme is 0.005 (W/V)% or more, but even if it is 0.001 (W/V)% or less, satisfactory results will certainly be obtained by prolonged treatment. A 20 (W/V)% urea solution or a solution containing the proteolytic enzyme alone does not provide satisfactory results within 6 hours.

Table 3 shows the relative durations of time required for removal of proteinaceous matter artificially deposited on each of contact lenses, by using each of 0.5 (W/V)% proteolytic enzyme solution containing a sulfhydryl compound, for example 1 (W/V)% of sodium hydrosulfite, and 0.9 (W/V)% of sodium chloride, with or without addition of 20 to 35 (W/V)% of urea, adjusted to pH 7.0 with 1 N-sodium hydroxide.

TABLE 3

| Enzyme | Concentration of urea | | Time required for removal of proteinaceous matter |
| --- | --- | --- | --- |
| Proteinase | 0.5(W/V)% | 20(W/V)% | About 4 hours |
| " | " | Not added | >12 hours |
| Papain | " | 20(W/V)% | About 4 hours |
| " | " | Not added | >12 hours |
| Pronase P | " | 35(W/V)% | About ¼ hours |
| " | " | 20(W/V)% | About 4 hours |
| " | " | Not added | >12 hours |

As apparent from Table 3, it took 12 hours or more to remove the proteinaceous matter artificially deposited on contact lenses by a 0.5 (W/V)% solution of the proteolytic enzyme. However, the synergistic effect obtainable by the combined use of urea and such enzyme was surprising. Proteinaceous matter was removed, for example in about 15 minutes, with 35 (W/V)% of urea and in about 4 hours by the addition of 20 (W/V)% of urea. On the other hand, a solution containing only sodium sulfite and 35 (W/V)% of urea without a proteolytic enzyme was still able to remove proteinaceous matter, but such a solution containing only 20 (W/V)% of urea was not able to remove proteinaceous matter at room temperature.

In order to clarify the combined effect of proteolytic enzyme with urea, the following experiments were conducted.

Basic formula of the examined compositions:

| | (W/V)% |
| --- | --- |
| Proteolytic enzyme | 0.005–0.5 |
| Sodium sulfite | 0.34 |
| Sodium hydrogensulfite | 0.66 |
| Disodium hydrogenphosphate | 0.4 |
| Sodium dihydrogenphosphate | 0.1 |
| Purified water | to 100 |

In the experiments compositions which complied with the basic formula were compared with a formula containing 20 (W/V)% of urea added in the basic formula.

Each contact lens, contaminated artificially with lisozyme, was divided into two equal pieces for the purpose of minimizing experimental errors as far as possible.

Into each 5 ml of each composition, was soaked the half piece of a soft contact lens for 15 hours and then the degree of cleaning of the lenses were compared with each other. The result is summarized in Table 4 in which papain, trypsin and Pronase p are used as proteolytic enzymes and the degree of cleaning is examined as in Table 1.

TABLE 4

| Enzyme | (W/V)% | Urea (W/V)% | Evaluation index of lens after treatment |
| --- | --- | --- | --- |
| Papain | 0.5 | 0 | +++ |
| " | 0.1 | 0 | ++ |
| " | 0.1 | 20 | +++ |
| " | 0.05 | 0 | + |
| " | 0.05 | 20 | +++ |
| " | 0.01 | 0 | − |
| " | 0.01 | 20 | ++ |
| Trypsin | 0.1 | 0 | ++ |
| " | 0.1 | 20 | +++ |
| " | 0.05 | 0 | + |
| " | 0.05 | 20 | +++ |
| " | 0.01 | 0 | − |
| " | 0.01 | 20 | ++ |
| Pronase p | 0.01 | 0 | ++ |
| " | 0.1 | 20 | +++ |
| " | 0.05 | 0 | + |
| " | 0.05 | 20 | +++ |
| " | 0.01 | 0 | − |
| " | 0.01 | 20 | +++ |
| " | 0.005 | 0 | − |
| " | 0.005 | 20 | ++ |

As clearly shown in Table 4, the cleaning effect appears markedly by addition of urea even in a concentration of a proteolytic enzyme which shows almost no cleaning effect in the absence of urea.

Thus, the combined use of a proteolytic enzyme and urea and/or an acid salt of guanidine provides an excellent synergistic effect in the presence of a sulfhydryl compound.

Depending on the cleaning composition used, soft contact lenses may be slightly swollen. However, when allowed to stand in physiological saline solution, they regain the original shapes, and their physical properties are not affected.

It is to be noted that the present invention may also be applied to hard contact and silicone contact lenses.

A buffer, chelating agent, etc. may be incorporated in the cleaning composition in accordance with the present invention.

The present invention will now be described in detail by way of the following examples.

EXAMPLE 1

A plastic container was filled with 2.5 g of urea and 0.1 g of sodium sulfite, followed by addition of a sufficient amount of water to make 5 ml. A soft contact lens artificially contaminated with lysozyme was immersed in this solution for about 10 minutes while the container was shaken from time to time. The lens was then rinsed, with gentle rubbing with fingers, and allowed to stand in physiological saline solution for 1 hour. By the above procedure there was obtained a cleaned lens.

EXAMPLE 2

A soft contact lens used and assumed to have proteinaceous matter was immersed for 30 minutes in a solution of 2.5 g of urea, 0.1 g of sodium metabisulfite and 0.02 g of a nonionic surfactant, i.e. polyoxyethylene nonyl phenyl ether (Niccol OP-30), which has been made up to 5 ml with water. The solution was shaken from time to time and thereafter the lens was treated as in Example 1. By the above procedure, there was obtained a cleaned lens.

EXAMPLE 3

To a mixture of 1.5 g urea and 0.15 g N-acetylcysteine was added a sufficient amount of water to make 5 ml and, after the solution was adjusted to pH 6.0 with sodium carbonate, a soft contact lens contaminated with lysozyme was put in the solution. The system was heated on a water bath for 5 minutes and thereafter treated as Example 1. By the above procedure, there was obtained a cleaned lens.

EXAMPLE 4

To a mixture of 2.5 g urea, 0.1 g sodium hydrogensulfite and 0.02 g polyoxyethylene nonyl phenyl ether (Niccol OP-30) was added a sufficient amount of water to make 5 ml and a silicone contact lens contaminated with lysozyme was immersed in the solution for 5 minutes, after which it was rinsed. By the above procedure, there was obtained a cleaned lens.

EXAMPLE 5

To a mixture of 2.5 g guanidine hydrochloride and 0.1 g of sodium sulfite was added a sufficient amount of water to make 5 ml, and a hard contact lens contaminated with lysozyme was immersed in the solution for 5 minutes, after which it was rinsed. By the above procedure, there was obtained a cleaned lens.

EXAMPLE 6

A plastic container was filled with 2.0 g of urea, 0.1 g of sodium hydrogen sulfite, 60 mg of sodium sulfite, 10 mg of sodium edetate, 0.1 g of sodium chloride and 50 mg of proteinase, followed by addition of a sufficient amount of water to make 10 ml. A soft contact lens used for 6 months and contaminated with proteinaceous matter was allowed to stand in this solution for about 3 hours, then taken out therefrom, rinsed, with gentle rubbing with fingers, and allowed to stand in physiological saline solution for 1 hour. By the above procedure, there was obtained a cleaned lens.

EXAMPLE 7

A plastic container was filled with 3.5 g of urea, 0.1 g of sodium metabisulfite, 10 mg of sodium edetate, 0.1 g of sodium chloride, 50 mg of sodium monohydrogen phosphate and 50 mg of proteinase, followed by addition of a sufficient amount of water to make 10 ml. A soft contact lens used for 3 months and contaminated with proteinaceous matter was allowed to stand in this solution for about 15 minutes and thereafter treated as in Example 1. By the above procedure, there was obtained a cleaned lens.

EXAMPLE 8

A plastic container was filled with 3.5 g of guanidine hydrochloride, 90 mg of sodium hydrogensulfite, 60 mg of sodium sulfite, 10 mg of sodium edetate, 0.1 g of sodium chloride and 50 mg of protease, followed by addition of a sufficient amount of water to make 10 ml. A soft contact lens contaminated with proteinaceous matter was allowed to stand in this solution for about 15 minutes, and thereafter treated as in Example 1. By the above procedure, there was obtained a cleaned lens.

EXAMPLE 9

A plastic container was filled with 2.0 g of urea, 0.1 g of cysteine hydrochloride, 10 mg of sodium edetate, 0.1 g of sodium chloride and 30 mg of papain, followed by addition of a sufficient amount of water to make 10 ml and adjusted to pH 6.5 by 1 N-sodium hydroxide. A soft contact lens contaminated with proteinaceous matter was allowed to stand in this solution for 3 hours and thereafter treated as in Example 1. By the above procedure, there was obtained a cleaned lens.

EXAMPLE 10

A plastic container was filled with 2.0 g of guanidine hydrochloride, 0.1 g of sodium hydrogensulfite, 60 mg of sodium sulfite and 10 mg of pronase P, followed by addition of a sufficient amount of water to make 10 ml. A silicone contact lens artificially contaminated with lysozyme was allowed to stand in this solution for 3 hours and thereafter treated as in Example 1. By the above procedure, there was obtained a cleaned lens.

EXAMPLE 11

A hard contact lens artificially contaminated with lysozyme was treated in a cleaning composition of the same recipe as that of Example 5, and there was obtained a cleaned lens.

We claim:

1. A composition for cleaning contact lenses contaminated with proteinaceous matter by immersing the lenses in an aqueous hypertonic solution, said composition comprising urea or an acid salt of guanidine in an amount sufficient to make the solution hypertonic, an effective amount of a sulfhydryl group-containing compound to reduce intermolecular or intramolecular S—S bonds in the contaminant proteinaceous matter and a proteolytic enzyme in an amount sufficient to have a synergistic cleaning effect with the urea or the acid salt of guanidine mentioned above.

2. A composition according to claim 1 which comprises a sufficient amount of urea or an acid salt of guanidine to make a concentration from 10 to 60 W/V percent, a sufficient amount of a sulfhydryl group-containing compound to make a concentration from 0.1 to 5 W/V percent and a sufficient amount of a proteolytic enzyme to make a concentration from 0.001 to 5 W/V percent, in the aqueous solution.

3. A composition according to claim 2 which comprises a sufficient amount of urea or an acid salt of guanidine to make a concentration from 20 to 40 W/V percent, a sufficient amount of a sulfhydryl group-containing compound to make a concentration from 0.1 to 5 W/V percent and a sufficient amount of a proteolytic enzyme to make a concentration from 0.005 to 0.5 W/V percent in the aqueous solution.

4. A method for removing proteinaceous deposits on contact lenses which comprises immersing the lenses for a period of time sufficient to clean the lenses at room temperature or under heating, in an aqueous composition comprising urea or an acid salt of guanidine in an amount sufficient to make the composition hypertonic, an effective amount of a reducing agent of the group consisting of a sulfite, a pyrosulfite, a dithionite, sodium borohydride and a reducing organic water-soluble mercapto group-containing compound to reduce intermolecular or intramolecular S—S bonds in the contaminant proteinaceous matter, and rinsing the lenses to remove the urea or the acid salt of guanidine and the reducing agent from the lenses.

5. A method according to claim 1 in which the aqueous composition comprises urea or an acid salt of guanidine in a concentration from 5 W/V percent to saturation, and a reducing agent in a concentration from 0.01 to 20 W/V percent.

6. A method according to claim 4 in which the aqueous composition comprises urea in a concentration from 10 to 60 W/V percent and a sulfite in a concentration from 0.01 to 20 W/V percent.

7. A method according to claim 5 in which the aqueous composition comprises urea or an acid salt of guanidine in a concentration from 20 to 60 W/V percent and a reducing agent in a concentration from 0.1 to 10 W/V percent.

8. A method for removing proteinaceous deposits on contact lenses which comprises immersing the lenses for a period of time sufficient to clean the lenses in an aqueous composition comprising urea or an acid salt of guanidine in an amount sufficient to make the composition hypertonic, an effective amount of a sulfhydryl group-containing compound to reduce intermolecular or intramolecular S—S bonds in the contaminant proteinaceous matter and a proteolytic enzyme in an amount sufficient to have a synergistic cleaning effect with the urea or the acid salt of guanidine mentioned above, and rinsing the lenses to remove the urea or the acid salt of guanidine, the sulfhydryl group-containing compound and the proteolytic enzyme from the lenses.

9. A method according to claim 8 in which the aqueous composition comprises urea or an acid salt of guanidine in a concentration from 10 to 60 W/V percent, a sulfhydryl group-containing compound in a concentration from 0.1 to 5 W/V percent and a proteolytic enzyme in a concentration from 0.001 to 5 W/V percent.

10. A method according to claim 9 in which the aqueous composition comprises urea or an acid salt of guanidine in a concentration from 20 to 40 W/V percent, a sulfhydryl group-containing compound in a concentration from 0.1 to 5 W/V percent and a proteolytic enzyme in a concentration from 0.05 to 1.0 W/V percent.

* * * * *

UNITED STATES PATENT AND TRADEMARK OFFICE
CERTIFICATE OF CORRECTION

PATENT NO. : 4,285,738

DATED : August 25, 1981

INVENTOR(S) : Kazumi Ogata

It is certified that error appears in the above—identified patent and that said Letters Patent is hereby corrected as shown below:

Column 2, line 16:  change "An" to --As--.

Column 3, last line:  after "is", insert --very effective in the removal of proteinaceous matter lodged on contact lenses. The data also indicates that ascorbic acid was not effective.--

Table 2, line 2:  (after the table) change "proteineous" to --proteinaceous--.

Column 10, line 55:  change "1" to --4--.

Signed and Sealed this

Twenty-fourth Day of August 1982

|SEAL|

Attest:

GERALD J. MOSSINGHOFF

Attesting Officer          Commissioner of Patents and Trademarks